United States Patent [19]
Warner

[11] Patent Number: 5,902,318
[45] Date of Patent: May 11, 1999

[54] ARTICULATING FORCEPS HAVING A REFLECTIVE ELEMENT FOR VIEWING A SUBSTRATE

[76] Inventor: Thomas P. Warner, 3704 Merriweather La., Rochester Hills, Mich. 48306

[21] Appl. No.: 08/759,147

[22] Filed: Dec. 2, 1996

[51] Int. Cl.[6] .................................................... A61B 17/28
[52] U.S. Cl. ........................................... 606/205; 600/247
[58] Field of Search ..................................... 600/247, 248; 606/1, 205, 206; 433/82, 190, 162, 30, 31; 128/354

[56] References Cited

U.S. PATENT DOCUMENTS

| | | |
|---|---|---|
| 1,057,974 | 4/1913 | Miller . |
| 2,125,980 | 8/1938 | Basil ............................................ 32/69 |
| 4,219,331 | 8/1980 | Getz . |
| 4,225,667 | 9/1980 | Ruben . |
| 4,340,369 | 7/1982 | Steiner et al. . |
| 4,836,596 | 6/1989 | Owen ...................................... 294/99.2 |
| 5,015,252 | 5/1991 | Jones . |
| 5,076,784 | 12/1991 | Jensen . |
| 5,230,622 | 7/1993 | Brossoit . |
| 5,358,297 | 10/1994 | Coleman ................................ 294/99.2 |
| 5,370,648 | 12/1994 | Cracraft . |

*Primary Examiner*—Michael Buiz
*Assistant Examiner*—Daphna Shai
*Attorney, Agent, or Firm*—Bliss McGlynn, P.C.

[57] ABSTRACT

Articulating forceps having a reflective element for viewing a substrate include a pair of arms biased in a direction opposite one another and joined at their respective ends. The articulating forceps further include a pair of clamping members disposed opposite one another and biased toward one another by the pair of arms to their normally clamped position. A reflective member extends longitudinally relative to the pair of arms and is disposed spaced from, but adjacent to, the clamping member for viewing a substrate such as the patient's teeth or gums.

22 Claims, 6 Drawing Sheets

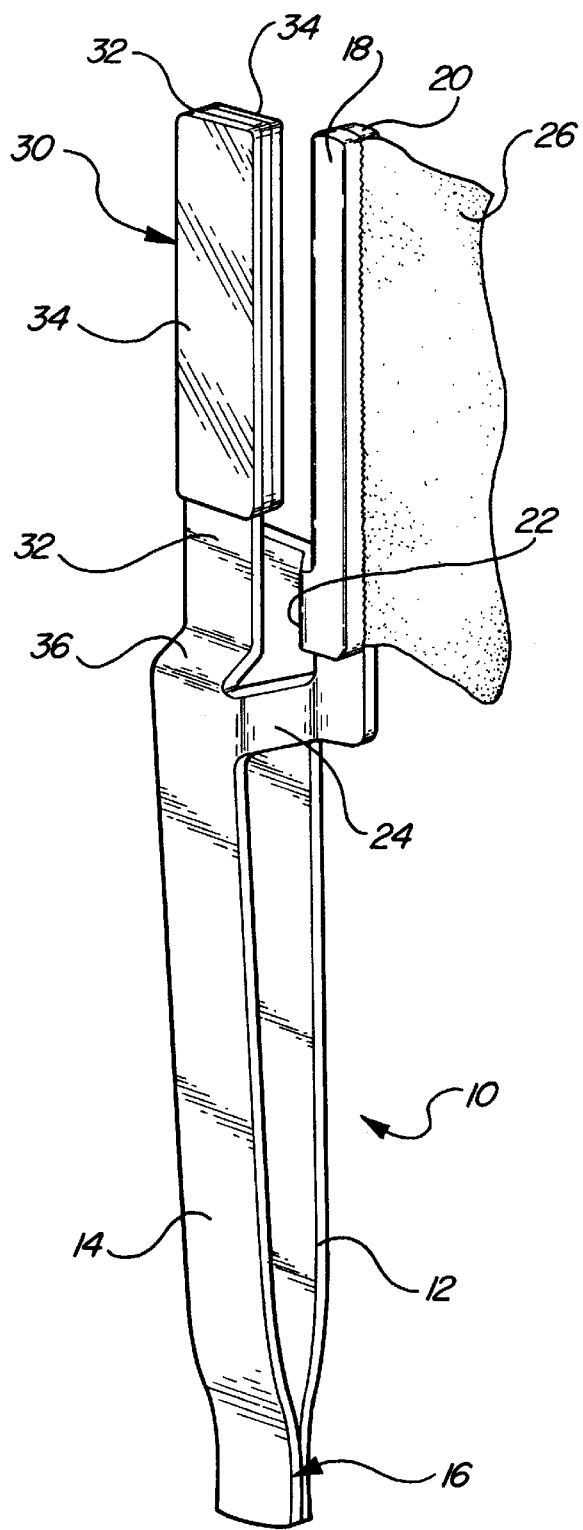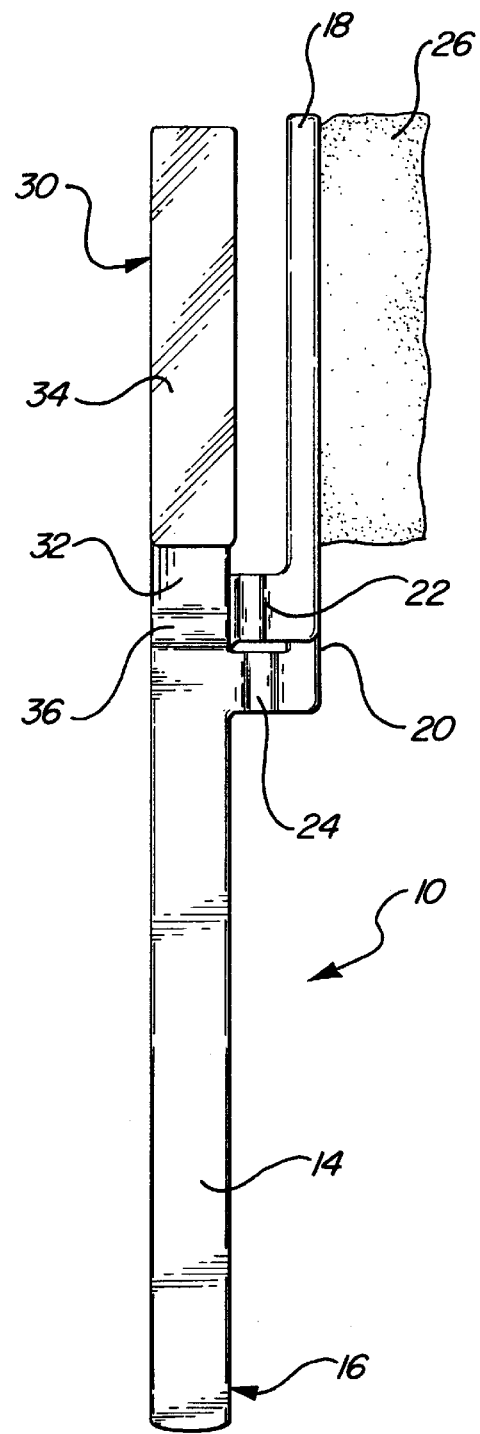
FIG-1
FIG-2

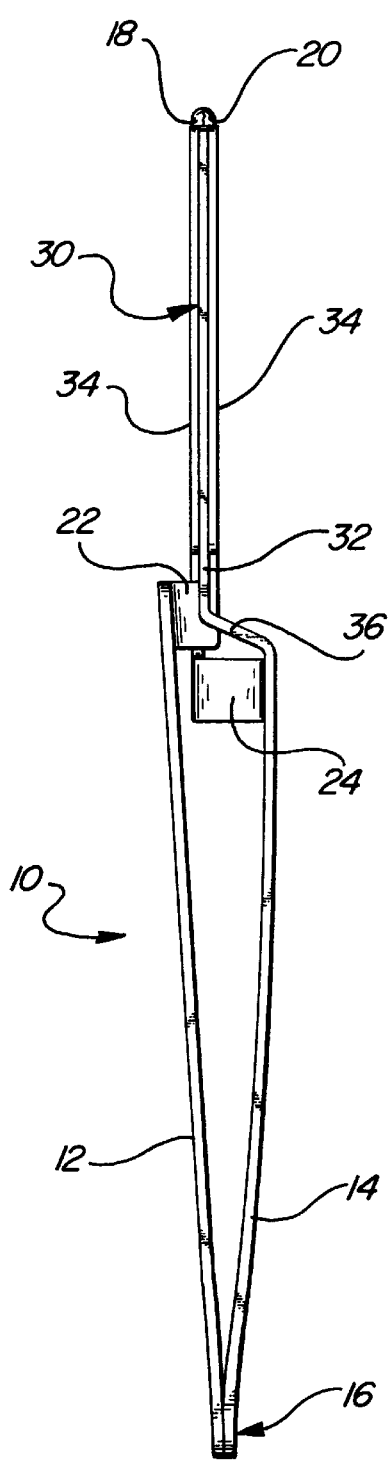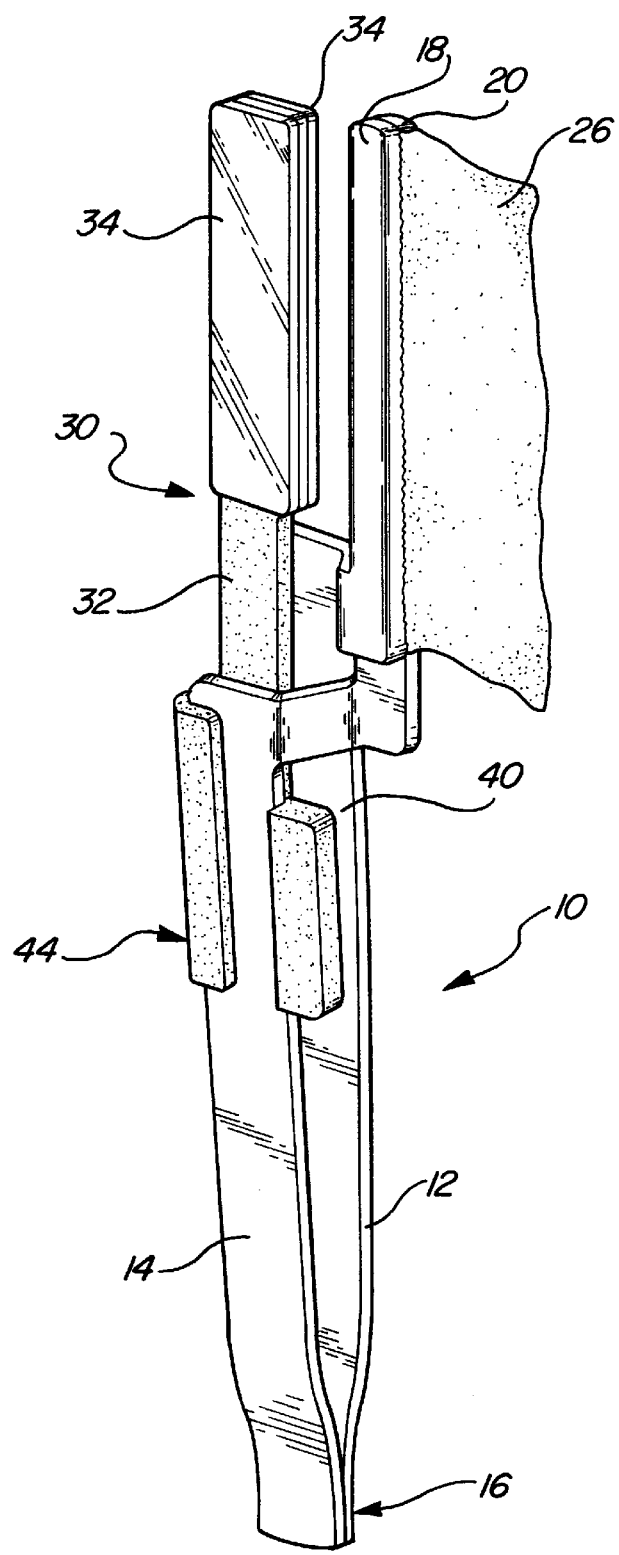

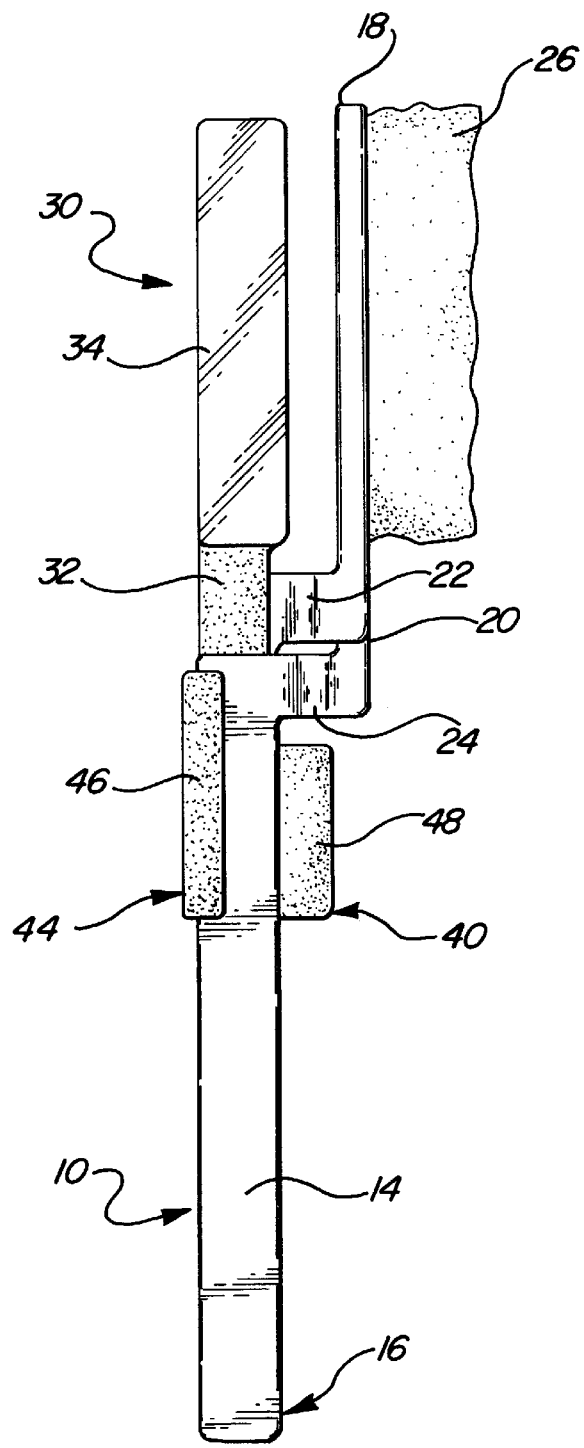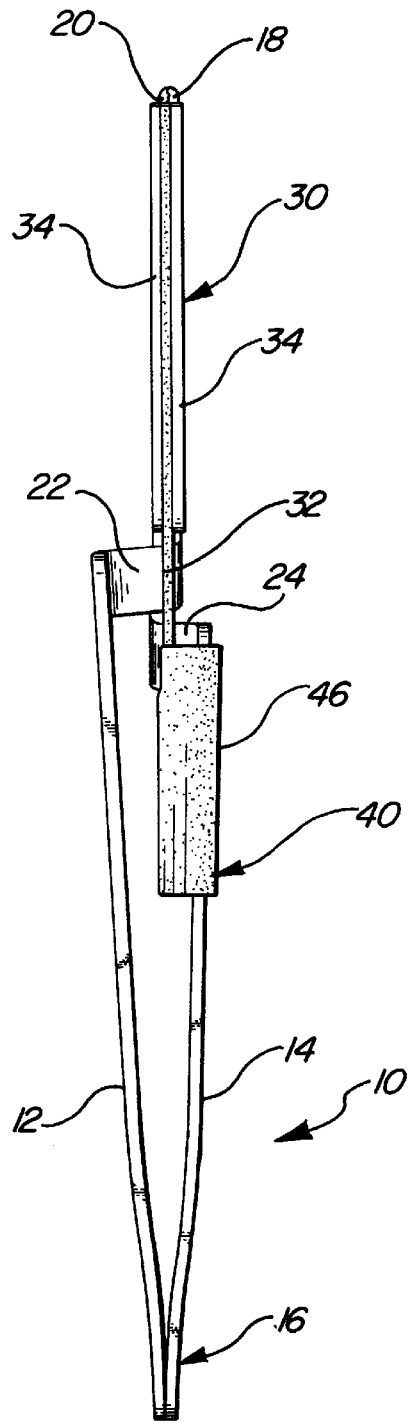
FIG-5                    FIG-6

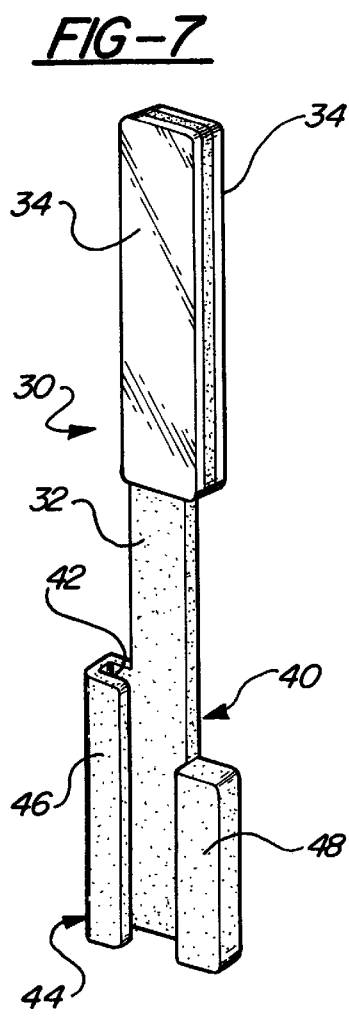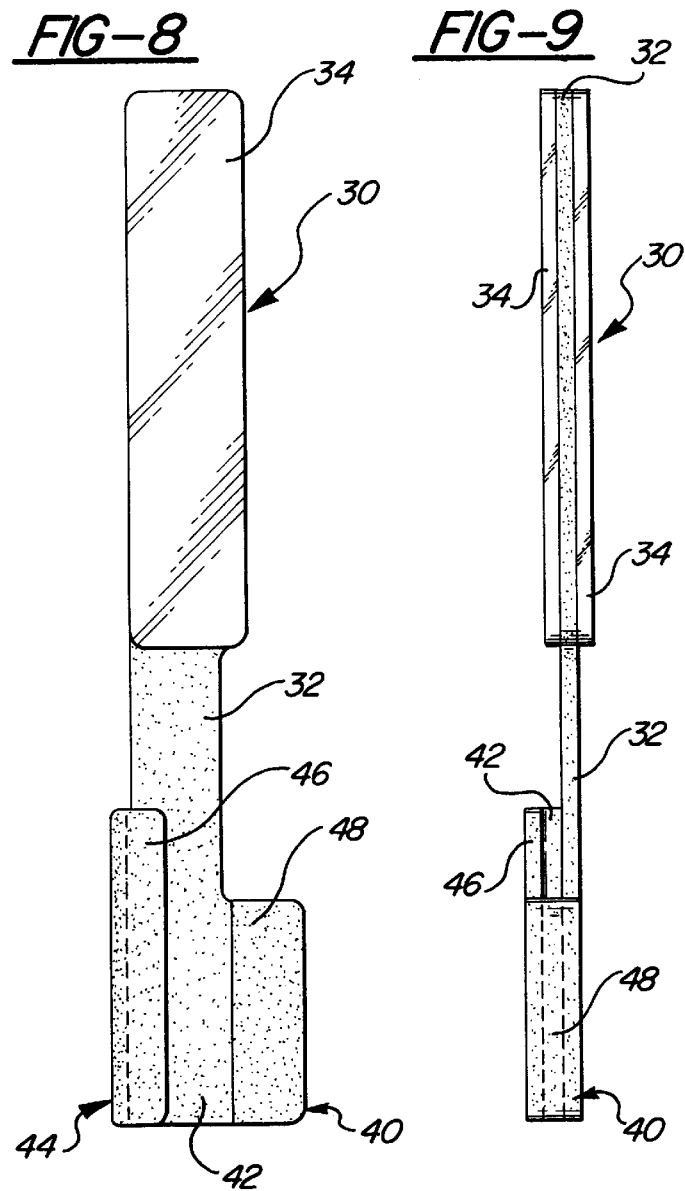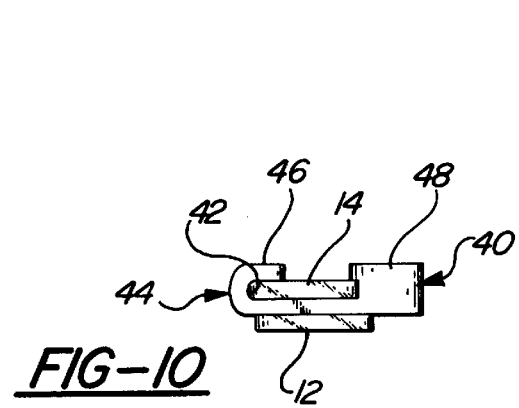

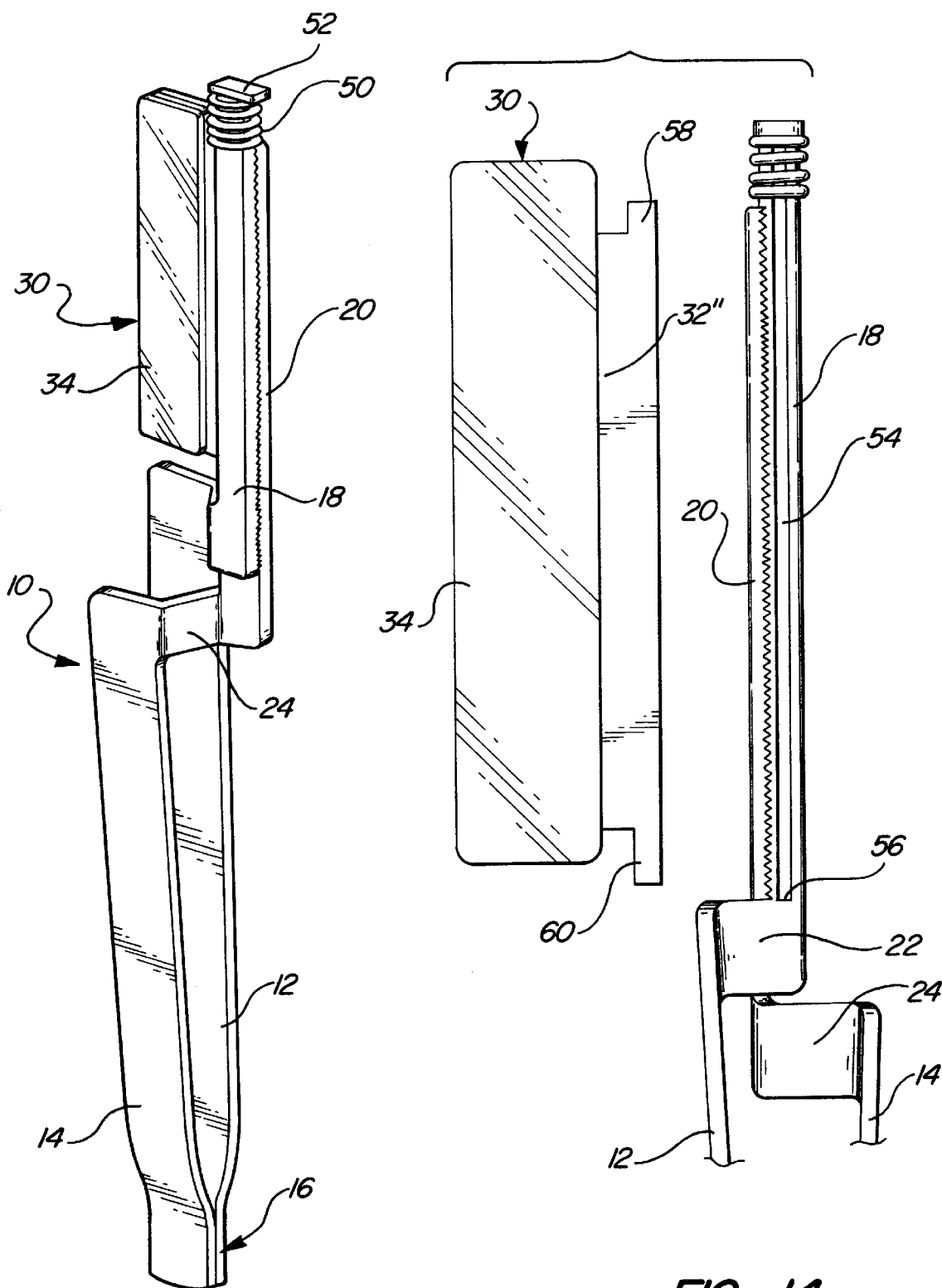

ly, to articulating forceps for use in the practice of dentistry and, more specifically, to articulating forceps having a reflective element for viewing a substrate such as the patient's teeth or gums.

5,902,318

ARTICULATING FORCEPS HAVING A REFLECTIVE ELEMENT FOR VIEWING A SUBSTRATE

BACKGROUND OF THE INVENTION

1. Field of the Invention

The invention relates, generally, to articulating forceps for use in the practice of dentistry and, more specifically, to articulating forceps having a reflective element for viewing a substrate such as the patient's teeth or gums.

2. Description of the Related Art

Dentists mark and then study the biting surfaces between opposing teeth in a patients mouth by performing a bite/occlusion test. This test is commonly employed, for example, after filling a tooth, inserting a crown, implant or a bridge as well as other such procedures to ensure that the contact between opposing teeth provides for a proper bite. The bite/occlusion test is necessary for the patient's comfort as well as ensuring that there is no improper contact between opposing teeth which could cause pressure, pain, fracture or infection to the patient.

The bite/occlusion test is performed using various types of marking paper, similar to carbon paper. The marking paper, known in the art as articulating paper, leaves a discernable pattern on the surface of the teeth which represents the contact points of the opposing teeth. A dentist inserts the articulating paper between the upper and lower teeth of a patient using what is commonly referred to as an articulating paper forceps. The articulating paper is clamped in the jaws of the forceps and the forceps is positioned in the patient's mouth such that the articulating paper is disposed between the upper and lower teeth. The patient is instructed to bite down on the paper thereby transferring indicator material from the paper to the teeth and showing the contact points between the upper and lower sets of teeth. Once the appropriate markings have been transferred to the teeth, the dentist removes the forceps and then inserts a mirror into the patient's mouth to observe the marking left on the teeth. In this way, the dentist makes adjustments as necessary until the patient's bite is correct.

However, there are certain common problems which are often faced by the dentist while performing a bite/occlusion test on dental patients. It is often the case that prior to the insertion of a mirror to visualize the bite pattern of the teeth, the patient either closes his mouth or swallows which often causes the patients tongue, cheek or saliva to alter or obliterate the marks left from the articulating paper on the teeth. When this happens, the test results are inconclusive and the procedure must be repeated. Usually, the bite/occlusion test must be performed multiple times before accurate results may be measured. This is unsatisfactory for both the dentist and the patient.

SUMMARY OF THE INVENTION AND ADVANTAGES

The present invention overcomes these disadvantages in the related art in an articulating forceps for use in the practice of dentistry. The articulating forceps have a reflective element for viewing a substrate such as the patients teeth, prosthesis, implants or gums and other soft tissue. The forceps include a pair of arms biased in a direction opposite one another and joined at one of their respective ends. A pair of clamping members are disposed opposite one another and biased toward one another by the pair of arms to their normally clamped position. A reflective member extends longitudinally relative to the pair of arms and may be disposed spaced from, but adjacent to, the clamping members. Alternatively, the reflective member may form a part of, or be carried by, the clamping members. The reflective member may be integral to the forceps or may be removably mounted thereto. The reflective member may include a reflective element, such as a mirror.

In this way, the marks left on the upper and lower teeth may be immediately viewed by the dentist after contact with the articulating paper and before the patient has had a chance to close his mouth or swallow or before the patient's tongue, cheek or sufficient saliva has been generated in the area of interest so as to obscure, alter or otherwise obliterate the impressions left by the paper. The articulating forceps of the present invention facilitate the elimination of multiple steps in the bite/occlusion test, simplifies the overall procedure and reduces the cost and time necessary to perform this test. In addition, the articulating forceps of the present invention increase the opportunity for the dentist to perform a successful bite/occlusion test the first time and, therefore, reduces the likelihood that there will be a need for additional, time consuming tests to be performed.

Other features and advantages of the present invention will be readily appreciated as the same becomes better understood after reading the subsequent description taken in conjunction with the accompanying drawings.

BRIEF DESCRIPTION OF THE DRAWINGS

FIG. 1 is a perspective view of one embodiment of the present invention;

FIG. 2 is an elevational view of the articulating forceps shown in FIG. 1;

FIG. 3 is a side view of the articulating forceps shown in FIG. 2;

FIG. 4 is a perspective view of another embodiment of the present invention;

FIG. 5 is an elevational view of the articulating forceps shown in FIG. 4;

FIG. 6 is a side view of the articulating forceps shown in FIG. 5;

FIG. 7 is a perspective view of the reflective member of the present invention;

FIG. 8 is an elevational view of the reflective member illustrated in FIG. 7;

FIG. 9 is a side view of the reflective member illustrated in FIG. 8;

FIG. 10 is an end view of the reflective member mounted to the forceps.

FIG. 13 is a perspective view of another embodiment of the present invention; and FIG. 14 is a partial side view of the articulating forceps shown in FIG. 13.

DESCRIPTION OF THE PREFERRED EMBODIMENT(S)

Figure 11:
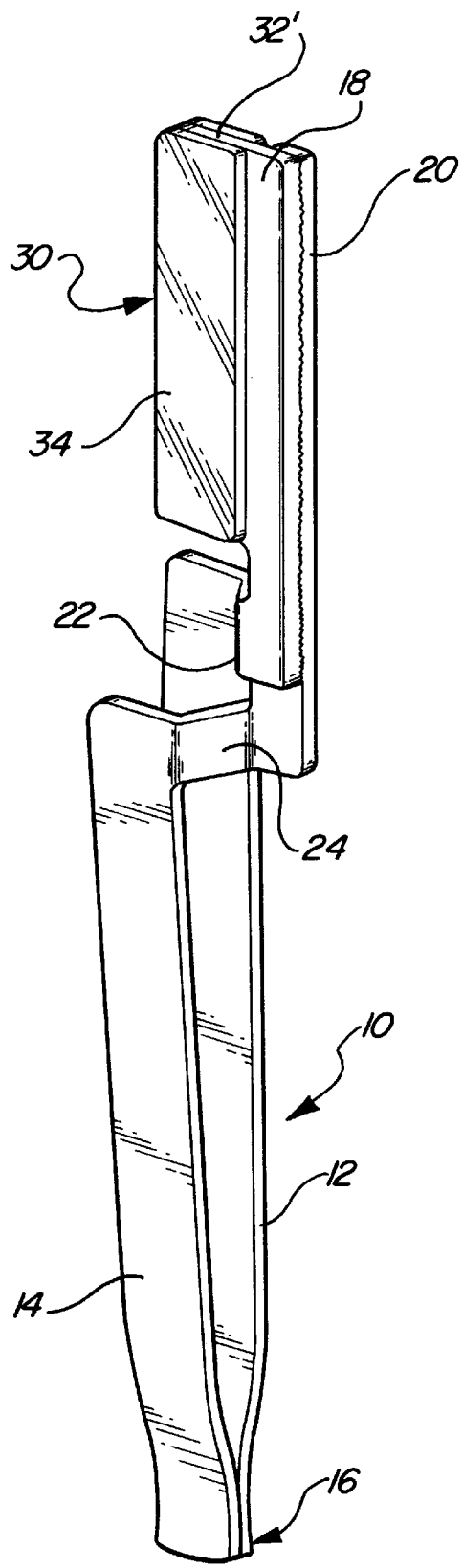
FIG. 11 is a perspective view of another embodiment of the present invention.

Articulating forceps are generally indicated at 10 in the Figures where like numerals are used to designate like structure throughout the drawings. The articulating forceps 10 are generally of the type employed in the practice of dentistry but persons of ordinary skill in the art will appreciate that the present invention as described in greater detail below may be utilized for other dental or medical procedures. Thus, the description of the present invention relative to dental procedures is for purposes of illustration and not by way of limitation. The articulating forceps 10 are typically manufactured from stainless steel and include a pair of arms 12, 14, biased in a direction opposite one another and joined at one of their respective ends as indicated, generally, at 16. A pair of clamping members 18, 20 are disposed opposite one another and biased toward one another by the pair of arms 12, 14 to their normally clamped position as is commonly known in the art.

The clamping member 18, 20 illustrated in the Figures are offset relative to the arms 12, 14 and interconnected to each respective arm by a pair of intermediate portions 22, 24 which extend generally transverse to the arms 12, 14. In its operative mode, the arms 12, 14 of the forceps 10 are gripped by the dentist and the clamping members 18, 20 are actuated by alternatingly pressing the arms 12, 14 toward each other thus opening the clamping members and releasing this pressure such that the arms 12, 14 move in a direction opposite one another thereby closing the clamping members 18, 20. As best shown in FIGS. 3 and 4, articulating paper 26 may be firmly held between the clamping members 18, 20 for performing the bite/occlusion test as described above. Alternatively, the forceps 10 may be used for any other suitable purpose.

The forceps 10 also include a reflective member, generally indicated at 30, which may be employed for viewing a substrate, such as a patient's teeth, prosthesis, implants or gums and other soft tissue. The reflective member 30 may be formed integrally with respect to the forceps 10 as illustrated in FIGS. 1 through 3, 11 and 12. In another embodiment, the reflective member 30 may be removably mountable to the forceps 10 as shown in FIGS. 4 through 6, 13 and 14 as will be discussed in greater detail below.

Referring now to FIGS. 1 through 3, the reflective member 30 extends longitudinally relative to the pair of arms 12 and 14 and is disposed spaced from, but adjacent to, the clamping members 18, 20 for viewing the substrate such as the patient's teeth and/or gums. The reflective member 30 includes a tongue 32 extending longitudinally relative to the arms 12, 14 and a reflective element 34 supported by the tongue 32 spaced from, but adjacent to, the pair of clamping members. As illustrated in FIGS. 1 through 3, the tongue 32 is manufactured from the same or similar material that is used for the arms 12, 14. While extending generally longitudinally relative to the arms 12, 14, as best shown in FIGS. 1 and 3, the tongue 32 may include an inclined portion 36 so that the reflective element 32 is disposed in substantially the same plane which contains the clamping members 18, 20.

The reflective element includes a mirror 34. The mirror 34 may be mounted to the tongue 32 using an adhesive or any other suitable means. Furthermore, the mirror 34 may be double-sided or, as best shown in FIGS. 1 and 3, a pair of mirrors 34 may be disposed on either side of the tongue 32. As illustrated in these Figures, the mirror 34 is substantially rectangular in shape with a major axis extending longitudinally relative to the pair of arms 12, 14 and parallel to the clamping members 18, 20. Alternatively, the reflective element 34 may include a circular mirror which is disposed in a plane parallel to a plane containing the pair of clamping members 18, 20.

Another embodiment of the reflective member 30 of the present invention is shown in FIGS. 4 through 10. As illustrated here, the reflective member 30 includes a body, generally indicated at 40, which is removably mounted to one of the arms 12 or 14 of the forceps 10. The body 40 defines a channel 42. The channel 42 cooperatively receives at least one of the pair of arms 14 such that the body 40 may be mounted to the forceps 10. The body 40 includes a tongue 32 which extends longitudinally relative to the arms 12, 14. The reflective member 30 includes a reflective element 34, such as a mirror, which is supported by the tongue 32 spaced from, but adjacent to, the clamping members 18, 20. The mirror 34 may be mounted to the tongue 32 using an adhesive or any other suitable means. Furthermore, and as shown in FIGS. 4, 7 and 9, a pair of mirrors 34 may be disposed on either side of the tongue 32.

The body 40 further includes a flexible lip, generally indicated at 44, which extends longitudinally relative to at least one of the arms 14 and is adapted to retain either one of the arms 12, 14 within the channel 42 when the reflective member 30 is mounted to the forceps 10. As best shown in FIGS. 7 through 10, the flexible lip 44 includes a pair of opposed lip portions 46, 48 which extend longitudinally relative to the arm 12 and act to define the channel 42. Further, the opposed lip portions 46, 48 also help to retain the arm 14 within the channel 42. The lip portion 46 is disposed so that it overlies a certain portion of the arm 14 when it is retained within the channel 42. The body 40 is made of a molded plastic and the opposed lip portions 46 and 48 are sized such that the arm 14 may be received within the channel 42 via "snap fit". Thus, in the embodiment illustrated in FIGS. 4 through 10, the reflective element may be repeatedly mounted to and/or removed from the forceps 10 as needed.

Figure 12:
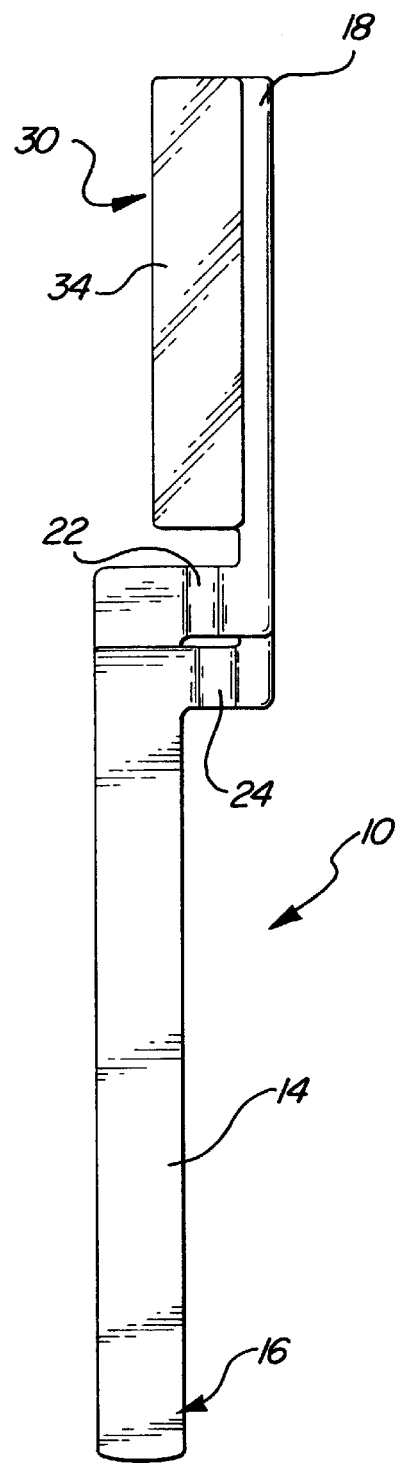
FIG. 12 is an elevational view of the articulating forceps shown in FIG. 11.

Still another embodiment of the articulating forceps 10 of the present invention is shown in FIGS. 11–14. As illustrated there, at least one of the clamping members 18 or 20 includes a reflective member 30 carried therewith for viewing a substrate. As shown in FIGS. 11 and 12, the reflective member 30 is formed integrally with the clamping member 18. As in the other embodiments discussed above, the reflective member 30 includes a mirror 34 which may be double sided or may be two mirrors 34 mounted to a support structure 32' extending from the clamping member 18. The mirror 34 is substantially rectangular in shape with a major axis extending longitudinally relative to the clamping members 18 and 20.

On the other hand and as shown in FIGS. 13–14, the articulating forceps 10 of the present invention may include a reflective member 30 which is removably mounted to the clamping members 18 or 20. In this embodiment, the clamping member 18 includes a biasing member 50 which is disposed at the distal end of the clamping member 18. The biasing member is a coiled spring 50 and is held on the clamping member 18 via a retainer 52. The clamping member 18 includes a groove 54 having at least one blind end 56. The reflective member 30 has a support structure 32" which includes first 58 and second 60 tabs. The first and second tabs 58, 60 are slidably received in the groove 54. The spring 50 biases the second tab into 60 into abutting contact with the blind end 56 of the groove 54. In this way, the reflective member 30 is releasbly retained in the groove 54 of the clamping member 18. As in the other embodiments, the reflective member 30 includes a mirror 34 which may be double sided or may include two mirrors mounted to the support structure 32". Similarly, the mirrors 34 are substantially rectangular in shape with a major axis extending longitudinally relative to the pair of clamping members.

The articulating forceps having a reflective element of the present invention substantially reduce the number of steps necessary to perform the bite/occlusion test and simplify the overall procedure for performing this test. Using the present invention, the articulating paper 26 is positioned between the upper and lower teeth using the forceps 10 and the patient is instructed to bite down. Without having to remove the forceps 10 and insert a separate implement having a mirror, the marks left on the upper and lower teeth may be immediately viewed by the dentist and before the patient has had a chance to close his mouth or swallow or before the patient's tongue, cheek or sufficient saliva has been generated in the area of interest so as to obscure, alter or otherwise obliterate the impressions left by the paper. Thus, the articulating forceps 10 having a reflective element 30 of the present invention increase the opportunity for the dentist to perform a successful bit/occlusion test the first time and reduce the likelihood that there will be a need for additional, time consuming tests to be performed. Furthermore, the dentist has the opportunity to significantly reduce the amount of articulating paper employed for such procedures and enjoys a concomitant reduction in costs.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

I claim:

1. Articulating forceps having a reflective element for viewing a substrate, said articulating forceps comprising:
    a pair of arms biased in a direction opposite one another and joined at one of their respective ends;
    a pair of clamping members disposed opposite one another and biased toward one another by said pair of arms to their normally clamped position; and
    a reflective member extending longitudinally relative to said pair of arms and disposed spaced from, but adjacent to, said pair of clamping members for viewing a substrate.

2. Articulating forceps as set forth in claim 1 wherein said reflective member includes a tongue extending longitudinally relative to said pair of arms and a reflective element supported by said tongue spaced from, but adjacent to, said pair of clamping members.

3. Articulating forceps as set forth in claim 1 wherein said reflective element includes a mirror.

4. Articulating forceps as set forth in claim 3 wherein said mirror is substantially rectangular in shape with a major axis extending longitudinally relative to said pair of arms and parallel to said pair of clamping members.

5. Articulating forceps as set forth in claim 1 wherein said reflective element includes a circular mirror disposed in a plane parallel to a plane containing said pair of clamping members.

6. Articulating forceps as set forth in claim 1 wherein said reflective member includes a body which is removably mountable to said forceps and which defines a channel, said channel cooperatively receiving at least one of said pair of arms to mount said body thereto.

7. Articulating forceps as set forth in claim 6 wherein said body includes a tongue extending longitudinally relative to at least one of said pair of arms, said reflective member including a reflective element supported by said tongue spaced from, but adjacent to, said pair of clamping members.

8. Articulating forceps as set forth in claim 7 wherein said body includes a flexible lip extending longitudinally relative to at least one of said pair of arms and adapted to retain said arm within said channel when said reflective member is mounted to said forceps.

9. Articulating forceps as set forth in claim 8 wherein said flexible lip includes a pair of opposed lip portions extending longitudinally relative to said arm which act together to define said channel and to retain said arm within said channel when said reflective member is mounted to said forceps.

10. Articulating forceps as set forth in claim 9 wherein said body is made of molded plastic.

11. Articulating forceps having a reflective element for viewing a substrate, said forceps comprising:
    a pair of arms biased in a direction opposite one another and joined at their respective ends;
    a pair of clamping members disposed opposite one another and biased toward one another by said pair of arms to their normally clamped position; and
    a reflective member formed integrally with respect to at least one of said pair of arms on said forceps and extending longitudinally relative to said pair of arms and disposed spaced from, but adjacent to, said pair of clamping members for viewing a substrate.

12. Articulating forceps as set forth in claim 11 wherein said reflective member includes a tongue extending longitudinally relative to said pair of arms and a reflective element supported by said tongue spaced from, but adjacent to, said pair of clamping members.

13. Articulating forceps as set forth in claim 11 wherein said reflective element includes a mirror.

14. Articulating forceps as set forth in claim 13 wherein said mirror is substantially rectangular in shape with a major axis extending longitudinally relative to said pair of arms and parallel to said pair of clamping members.

15. Articulating forceps as set forth in claim 11 wherein said reflective element includes a circular mirror disposed in a plane parallel to a plane containing said pair of clamping members.

16. Articulating forceps having a reflective element for viewing a substrate, said articulating forceps comprising:
    a pair of arms biased in a direction opposite one another and joined at their respective ends;
    a pair of clamping members disposed opposite one another and biased toward one another by said pair of arms to their normally clamped position, at least one of said clamping members including a separate reflective member formed integrally with at least one of said clamping members for viewing a substrate.

17. Articulating forceps as set forth in claim 16 wherein said reflective member includes a mirror.

18. Articulating forceps as set forth in claim 12 wherein said mirror is substantially rectangular in shape with a major axis extending longitudinally relative to said pair of clamping members.

19. Articulating forceps having a reflective element for viewing a substrate, said articulating forceps comprising:
    a pair of arms biased in a direction opposite one another and joined at their respective ends;
    a pair of clamping members disposed opposite one another and biased toward one another by said pair of arms to their normally clamped position, at least one of said clamping members including a reflective member removably mounted thereto for viewing a substrate.

20. An articulating forceps as set forth in claim 19 wherein said at least one clamping member includes a biasing member disposed at the distal end thereof and a groove having at least one blind end, said reflective member including first and second tabs slidably received in said groove, said biasing member biasing said second tab into abutting contact with said at least one blind end of said groove to releasably retain said reflective member with said at least one clamping member.

21. An articulating forceps as set forth in claim 19 wherein said reflective member includes a mirror.

22. An articulating forceps as set forth in claim 21 wherein said mirror is substantially rectangular in shape with a major axis extending longitudinally relative to said pair of clamping members.

* * * * *